US009264841B2

(12) United States Patent
Nonaka

(10) Patent No.: US 9,264,841 B2
(45) Date of Patent: Feb. 16, 2016

(54) WIRELESS COMMUNICATION APPARATUS, WIRELESS COMMUNICATION SYSTEM, WIRELESS COMMUNICATION METHOD, X-RAY SENSOR, AND PROGRAM STORAGE MEDIUM

(75) Inventor: Hideki Nonaka, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 167 days.

(21) Appl. No.: 13/207,238

(22) Filed: Aug. 10, 2011

(65) Prior Publication Data

US 2012/0045991 A1    Feb. 23, 2012

(30) Foreign Application Priority Data

Aug. 17, 2010    (JP) .................................. 2010-182176

(51) Int. Cl.
  *H04B 7/00*    (2006.01)
  *H04W 4/00*    (2009.01)
  *H04W 76/02*   (2009.01)
  *A61B 6/00*    (2006.01)

(52) U.S. Cl.
  CPC ............... *H04W 4/00* (2013.01); *A61B 6/4494* (2013.01); *H04W 4/008* (2013.01); *H04W 76/02* (2013.01)

(58) Field of Classification Search
  CPC ....... H04W 4/00; H04W 88/06; H04W 84/12; H04W 40/00; H04Q 7/00
  USPC ........ 455/41.1, 41.2, 41.3, 525; 378/19, 98.8, 378/116
  See application file for complete search history.

(56) References Cited

U.S. PATENT DOCUMENTS

| 7,613,478 | B2 * | 11/2009 | Jabri ..................... A61B 5/7475 250/363.1 |
| 8,009,626 | B2 * | 8/2011 | Anjum .............. H04L 29/12254 370/328 |
| 8,611,501 | B2 * | 12/2013 | Kobayashi ........... A61B 6/4405 378/102 |
| 2001/0025275 | A1 * | 9/2001 | Tanaka ................... G06Q 50/06 705/412 |
| 2005/0054369 | A1 * | 3/2005 | Murakami ............ H04W 48/08 455/525 |

(Continued)

FOREIGN PATENT DOCUMENTS

| JP | 7-140255 A | 6/1995 |
| JP | 2003-172783 A | 6/2003 |

(Continued)

*Primary Examiner* — Wesley Kim
*Assistant Examiner* — Md Talukder
(74) *Attorney, Agent, or Firm* — Canon USA Inc., IP Division

(57) ABSTRACT

A wireless communication apparatus includes an X-ray sensor that transmits X-ray image data, a wireless access point that receives the X-ray image data from the X-ray sensor by wireless communication, and an entry apparatus that communicates with the X-ray sensor by short-range communication. A wireless setting apparatus sets wireless communication parameters for starting the wireless communication between the X-ray sensor and the wireless access point to the wireless access point and sets the same wireless communication parameters as those set to the wireless access point to the X-ray sensor by performing short-range wireless communication from the entry device.

17 Claims, 4 Drawing Sheets

(56) References Cited

U.S. PATENT DOCUMENTS

| | | | |
|---|---|---|---|
| 2005/0211908 A1* | 9/2005 | Dieras | A61B 6/145 250/370.09 |
| 2006/0008054 A1* | 1/2006 | Ohara | 378/114 |
| 2006/0215892 A1* | 9/2006 | Ohara | A61B 6/00 382/128 |
| 2006/0242094 A1* | 10/2006 | Tamakoshi | A61B 6/4233 706/23 |
| 2006/0280381 A1* | 12/2006 | Iwakiri | G01T 7/00 382/305 |
| 2007/0146130 A1* | 6/2007 | Hannemann | A61B 6/145 340/539.22 |
| 2007/0260134 A1* | 11/2007 | Serceki | A61B 6/00 600/407 |
| 2008/0003989 A1* | 1/2008 | Vau | G06F 17/30014 455/414.3 |
| 2008/0029707 A1* | 2/2008 | Kari | A61B 6/4405 250/370.09 |
| 2009/0006211 A1* | 1/2009 | Perry | G06Q 30/02 705/14.66 |
| 2009/0130983 A1* | 5/2009 | Venturino | A61B 6/00 455/66.1 |
| 2009/0220048 A1* | 9/2009 | Ohta | A61B 6/4233 378/98 |
| 2010/0004023 A1* | 1/2010 | Jabri | A61B 5/7475 455/556.1 |
| 2010/0130165 A1* | 5/2010 | Snyder | G06F 21/88 455/410 |
| 2010/0195589 A1* | 8/2010 | Moritomo | H04L 12/66 370/329 |
| 2010/0246772 A1* | 9/2010 | Park | A61B 6/4233 378/98.8 |
| 2011/0111703 A1* | 5/2011 | Claverie | H04N 5/32 455/66.1 |
| 2011/0116486 A1* | 5/2011 | Tachikawa | A61B 6/4494 370/338 |
| 2011/0150182 A1* | 6/2011 | Omura | A61B 6/4405 378/98.5 |
| 2011/0261804 A1* | 10/2011 | Antoine | H04L 29/12594 370/342 |
| 2011/0306882 A1* | 12/2011 | Hannon | A61B 6/4494 600/443 |
| 2012/0045991 A1* | 2/2012 | Nonaka | H04W 4/00 455/41.2 |
| 2013/0010928 A1* | 1/2013 | Hannon | A61B 6/4405 378/98 |
| 2013/0073406 A1* | 3/2013 | Gazdzinski | G06Q 10/08 705/21 |
| 2013/0102245 A1* | 4/2013 | Ohguri | A61B 6/548 455/39 |
| 2013/0195251 A1* | 8/2013 | Saigusa | H05G 1/30 378/101 |
| 2013/0329860 A1* | 12/2013 | Nonaka | A61B 6/548 378/91 |
| 2014/0177806 A1* | 6/2014 | Tachikawa | A61B 6/4494 378/114 |

FOREIGN PATENT DOCUMENTS

| | | |
|---|---|---|
| JP | 2005-150895 A | 6/2005 |
| JP | 2009-533905 A | 9/2009 |

* cited by examiner

WIRELESS COMMUNICATION APPARATUS, WIRELESS COMMUNICATION SYSTEM, WIRELESS COMMUNICATION METHOD, X-RAY SENSOR, AND PROGRAM STORAGE MEDIUM

BACKGROUND OF THE INVENTION

1. Field of the Invention

The present invention relates to wireless communication, and in particular, relates to a technology suitable for setting wireless communication at the time of installation.

2. Description of the Related Art

Conventionally, digital X-ray imaging apparatuses have been commercialized. The digital X-ray imaging apparatus generates X-rays to acquire X-ray image data from an X-ray sensor, performs analog-to-digital (A/D) conversion on the X-ray image data into digital X-ray image data, and performs image processing on the digital X-ray image data for diagnosis. An arrangement of a conventional X-ray imaging apparatus is illustrated in FIG. 3, for example. As illustrated in FIG. 3, in the conventional digital X-ray imaging apparatus, an X-ray sensor 1001 is generally installed on an upright stand or a table and is tethered with a cable to be used.

However, depending on an image capture method, it is necessary to capture X-ray images at a free position without fixing the X-ray sensor. In response to such a necessity a portable X-ray sensor has been proposed. For example, Japanese Patent Application Laid-Open No. 2003-172783 discusses an X-ray imaging apparatus including a thin and lightweight type X-ray sensor which is easy to handle. Japanese Patent Application Laid-Open No. 7-140255 discusses an X-ray imaging apparatus in which an X-ray sensor and a synchronous repeater are wirelessly connected to eliminate installation limitations of an X-ray sensor 1101 due to a cable, as illustrated in FIG. 4.

To provide a high-quality X-ray image, the pixel pitch of the X-ray sensor is about 100 to 200 μm and a 16-bit density resolution is used. If an image region size is 17"*14" (43*35 cm), the data size constituting one image becomes generally 7.5 to 30 megabytes. To display an X-ray image at a speed of several seconds on a display after capturing the X-ray image at a free position and acquiring X-ray image data of the above size, a wireless communication unit is also required to be correspondingly fast. To easily realize such a high speed performance, a radio frequency (RF) wave is used for wireless communication.

Regarding RF waves, however, local RF regulations differ according to countries and regions, and available frequency bands are regulated for each country or region. Thus, individual and specific RF wave setting is required for an X-ray imaging apparatus according to the country or the region. Therefore, the RF wave setting has conventionally been performed on the apparatus according to a destination or an installation site at the time of shipment or the installation by human work.

However, the radio frequency (RF) wave settings established by human work are prone to the occurrence of operational error. If an operational error occurs and RF wave communications is set to a band out of regulation, the X-ray sensor may fail to operate properly and/or it may operate outside of regulated conditions which may be against local or regional laws.

SUMMARY OF THE INVENTION

The present invention is directed to a technique capable of easily starting communication with a radio wave setting corresponding to the region of use.

According to an aspect of the present invention, a wireless communication apparatus capable of transmitting wireless communication parameters with an access point to an X-ray sensor includes a setting unit configured to acquire region information from the access point to set the wireless communication parameters within a range of a channel corresponding to the region information, and an entry unit configured to transmit the wireless communication parameters to the X-ray sensor by short-range wireless communication.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
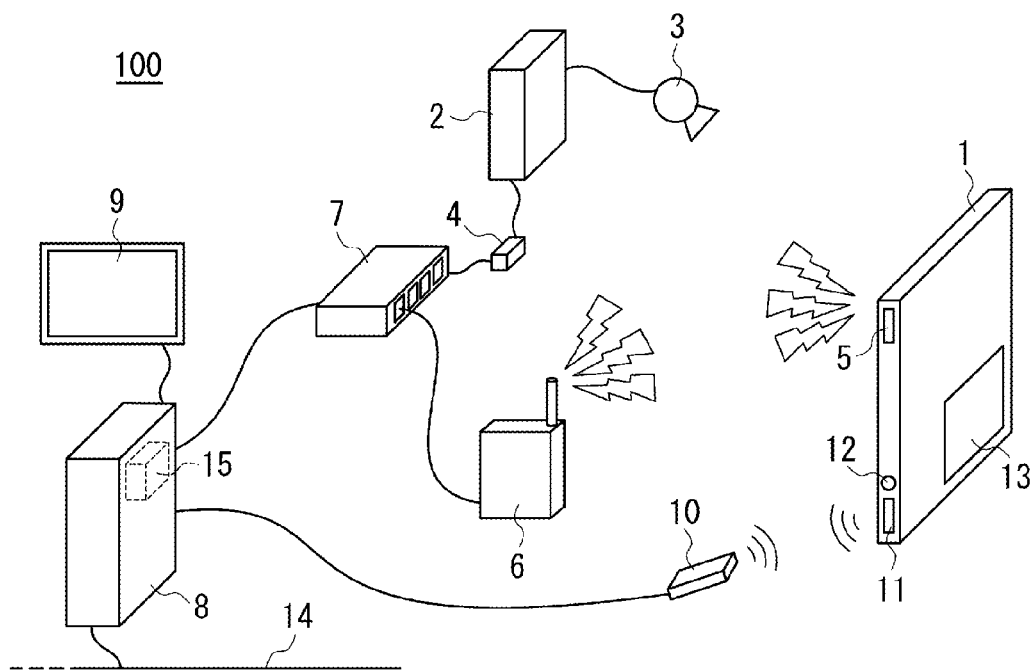
FIG. 1 illustrates an example of an overall configuration of a wireless X-ray imaging apparatus according to an exemplary embodiment of the present invention.

FIG. 1 illustrates an example of an overall configuration of a wireless X-ray imaging apparatus 100 according to an exemplary embodiment of the present invention. The wireless X-ray imaging apparatus 100 in the present exemplary embodiment includes an X-ray sensor 1, a wireless access point (AP) 6, an entry apparatus 10, and a wireless setting apparatus 15.

In FIG. 1, the X-ray sensor 1 detects X-rays generated by an X-ray generation apparatus 3 according to control of an X-ray control apparatus 2 to generate digital X-ray image data. An X-ray interface apparatus 4 is used to connect the X-ray control apparatus 2 and a switching hub 7.

A RF wave communication unit 5 performs wireless communication with the wireless access point 6 based on wireless communication standards, such as, Institute of Electrical and Electronic Engineers (IEEE)802.11(a, b, g, n), or the like. The wireless access point 6 faces to the RF wave communication unit 5 to perform wireless communication by the RF wave and also performs communication with the X-ray interface apparatus 4 and an image processing apparatus 8 based on Ethernet (registered trademark). The switching hub 7 connects devices connected by Ethernet with a star topology. The image processing apparatus 8 is, for example, a personal computer (PC) and is used to perform image processing. A display apparatus 9 is used to display a digital X-ray image obtained after image processing or an operation screen.

The entry apparatus 10 is a device conforming to short-range wireless communication such as Infrared Data Association (IrDA) and is connected to the image processing apparatus 8 by a universal serial bus (USB) port or the like. A short-range wireless communication unit 11 is used to perform short-range wireless communication with the entry apparatus 10. A switch 12 is provided in the X-ray sensor 1 to start short-range wireless communication and a battery pack 13 (power source) supplies power to the X-ray sensor 1. A backbone network 14 is, for example, an in-hospital local area network (LAN) used to connect the image processing apparatus 8 to, for example, a picture archiving and communication system (PACS) in a known manner. The wireless setting apparatus 15 is implemented in the image processing apparatus 8 either as a dedicated hardware circuit, or as a software module operating in the image processing apparatus 8. The wireless setting apparatus 15 may also be implemented as a combination of hardware circuits and software modules connected to and operated by the image processing apparatus 8.

In the X-ray sensor 1, the RF wave communication unit 5 set not to operate in the initial state after shipment, in other words, in a state in which a region code to be set by a subsequent operation is not set. Thus, when the product is shipped, there is no need to perform RF wave settings based on a country or a region, which makes setting work unnecessary and also can reduce shipment place management of the product.

Thus, when the X-ray sensor is deployed for operation in a certain region, the X-ray sensor undergoes a setting sequence as follows. First, when the user presses the switch 12, the X-ray sensor 1 starts communication with the entry apparatus 10 via the short-range wireless communication unit 11. At this point, the entry apparatus 10 is in a standby state and starts a wireless communication parameter setting sequence using reception from the short-range wireless communication unit 11 of the X-ray sensor 1 as a trigger.

Figure 2:
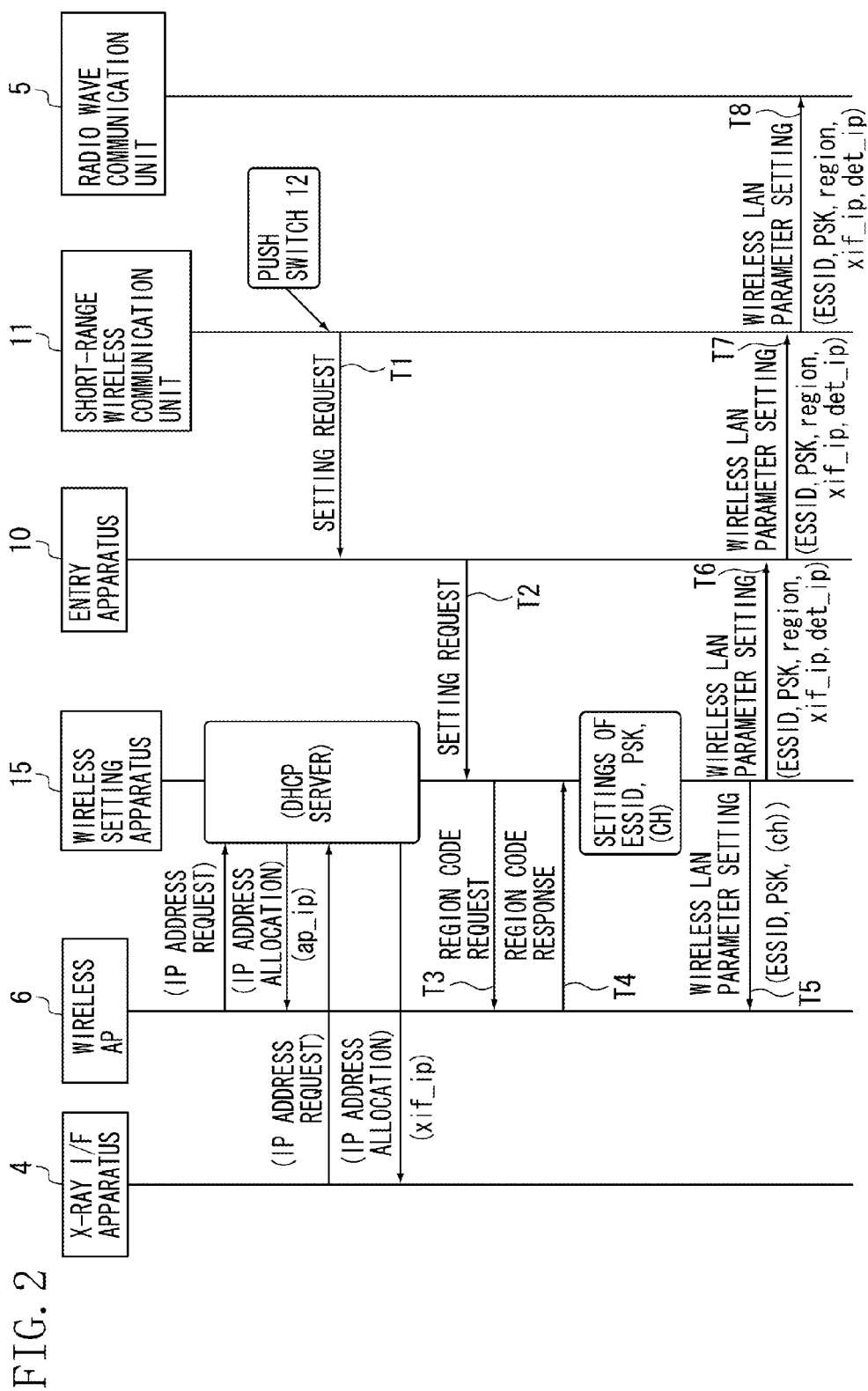
FIG. 2 is a timing chart illustrating a setting example of wireless communication parameters.

FIG. 2 is a timing chart illustrating an example of the setting sequence of the wireless communication parameters.

As illustrated in FIG. 2, with the switch 12 being pushed down, a setting request (T1) is transmitted from the short-range wireless communication unit 11 to the entry apparatus 10. Then, the entry apparatus 10 that has received the setting request transfers the setting request (T2) to the wireless setting apparatus 15 operating on the connected image processing apparatus 8. The wireless setting apparatus 15 performs various settings to establish a network connection of each unit constituting the wireless X-ray imaging apparatus 100.

Figure 3:
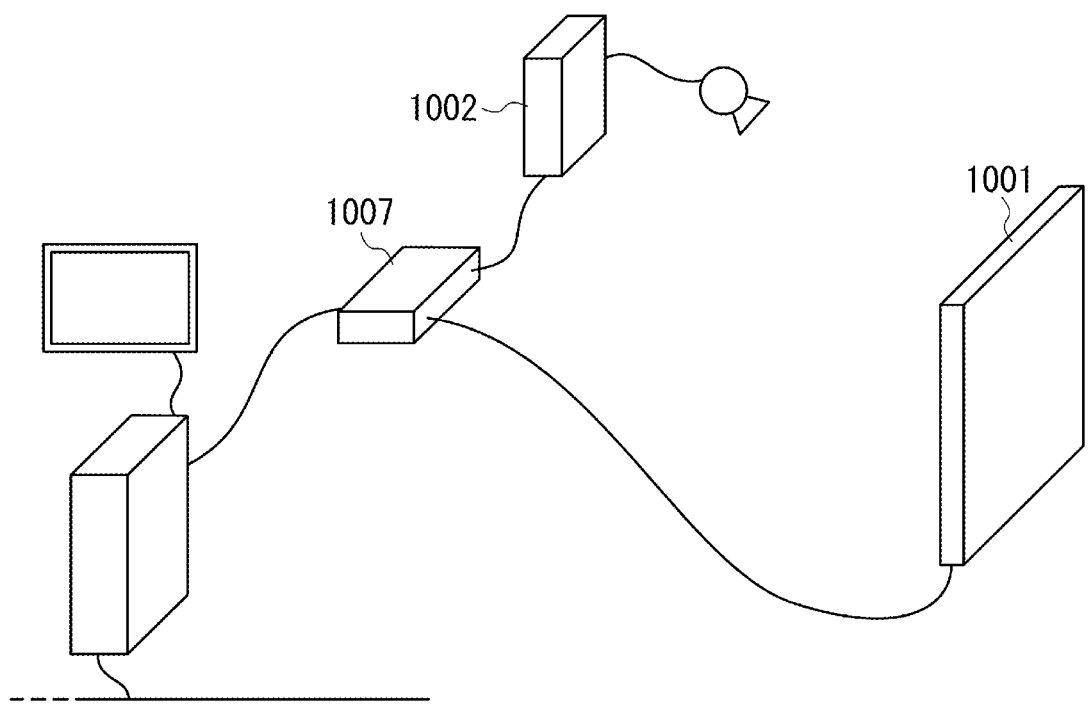
FIG. 3 illustrates an example of an overall configuration of a conventional wired X-ray imaging apparatus.
Figure 4:
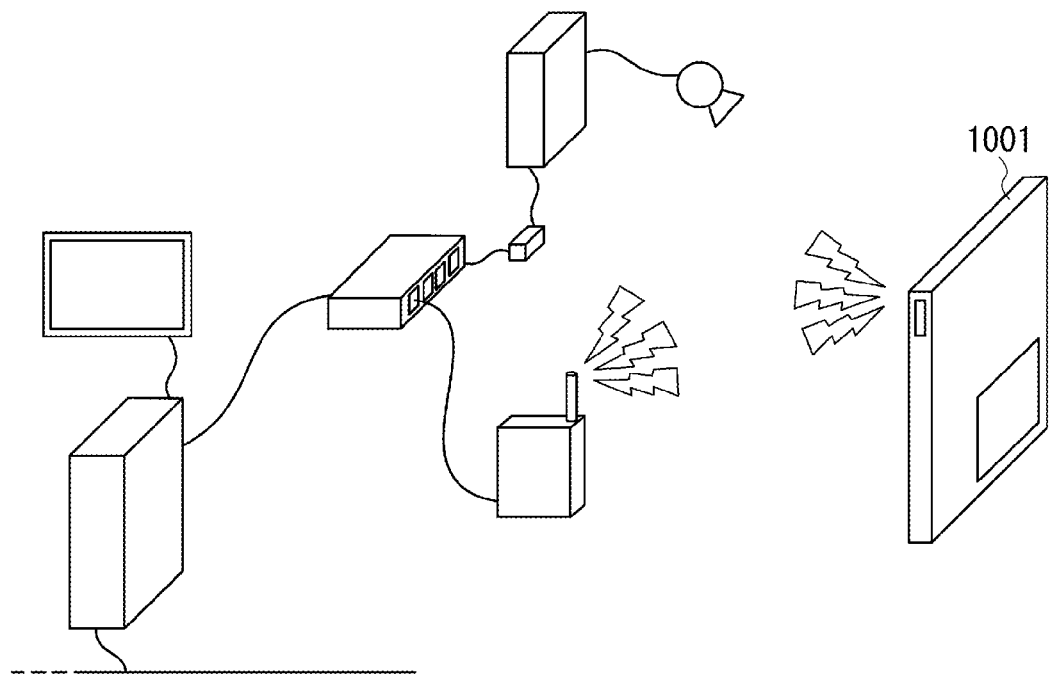
FIG. 4 illustrates an example of an overall configuration of a conventional wireless X-ray imaging apparatus.

To capture an X-ray image by the X-ray sensor 1, it is necessary to emit X-rays for exposure from the X-ray generation apparatus 3 in synchronization with an internal operation of the X-ray sensor 1. For synchronous exposure of X-rays, it is necessary to exchange an X-ray synchronization signal between the X-ray sensor 1 and the X-ray control apparatus 2. For example, in the case of a wired connection X-ray imaging apparatus as illustrated in FIG. 3, an X-ray synchronization signal is exchanged between the X-ray sensor 1001 and an X-ray control apparatus 1002 via a synchronous repeater 1007.

In the present exemplary embodiment, by contrast, it is necessary to exchange an X-ray synchronization signal between the X-ray sensor 1 and the X-ray control apparatus 2 by wireless communication. Thus, the X-ray interface apparatus 4 connected to the X-ray control apparatus 2 mutually converts an X-ray synchronization signal connecting to the X-ray control apparatus 2 and a protocol used for communication on Ethernet.

For the X-ray sensor 1 to access the X-ray interface apparatus 4, it is necessary to transmit an Internet Protocol (IP) address (xif_ip) of the X-ray interface apparatus 4 to the X-ray sensor 1. It is also necessary to allocate the IP address (ap_ip) to the wireless access point 6 to request a region code from the wireless access point 6 or to set wireless communication parameters thereto. The access is enabled by setting fixed IP addresses to the X-ray interface apparatus 4 and the wireless access point 6 in advance and setting information thereof to the wireless setting apparatus 15.

The X-ray interface apparatus 4 and the wireless access point 6 can operate as dynamic host configuration protocol (DHCP) clients by implementing a DHCP server function in the wireless setting apparatus 15. If, as illustrated in FIG. 2, no IP address is set to the X-ray interface apparatus 4 and the wireless access point 6, which are DHCP clients, an IP address request is transmitted to the wireless setting apparatus 15 and the wireless setting apparatus 15 allocates IP addresses as a response thereof. Accordingly, IP addresses can easily be set to the X-ray interface apparatus 4 and the wireless access point 6, so that the work load on a user can be reduced. Moreover, the operation can be caused in timing independent of the wireless communication parameter setting sequence.

Next, the wireless setting apparatus 15 that has received the setting request requests the region code (T3), which is region information of wireless communication, from the wireless access point 6 connected to the image processing apparatus 8. The wireless access point 6 that has received the request of the region code transmits the region code contained therein as a response (T4). The wireless access point 6 sets a RF wave corresponding to the contained region code. More specifically, the wireless access point 6 is set so as not to operate at frequencies other than available frequencies (channels), so that the apparatus can comply with the RF regulation of the region of use.

Regarding channels of 2.4 GHz band in North America, for example, ch1 of the center frequency 2.412 GHz to ch11 of the center frequency 2.462 GHz are available. In Japan and Europe, on the other hand, ch1 to ch13 of the center frequency 2.472 GHz are available, thus available channels are different from country to country or from region to region. The wireless access point 6 selects the channel to use from the channel range corresponding to the contained region code.

Further, to use the wireless access point 6, it is necessary to set service set identifier (SSID) serving as an identifier of the wireless network and an encryption key (PSK) for concealment of information to both the wireless access point 6 and the X-ray sensor 1. As illustrated in FIG. 1, the wireless access point 6 is connected to the image processing apparatus 8 with a wireline via the switching hub 7. Thus, the wireless setting apparatus 15 in the image processing apparatus 8 can perform remote settings of the wireless access point 6 using simple network management protocol (SNMP) or the like.

For the X-ray sensor 1, on the other hand, setting for the RF wave communication unit 5 is performed by short-range wireless communication of a method different from that of the RF wave communication unit 5 such as IrDA and TransferJet (trademark). Accordingly, the wireless access point 6 can be connected and set without needing cable connection.

For normal network equipment, the same wireless network can be constructed by performing the same settings of the SSID and the PSK on each device by the user. Thus, it is necessary for the user to recognize the SSID and the PSK for the network. In the present exemplary embodiment, by contrast, the wireless setting apparatus 15 sets both the wireless access point 6 and the RF wave communication unit 5 inside the X-ray sensor 1, which eliminates the work by the user to set the SSID and the PSK to each device.

The SSID and PSK may be set to the wireless setting apparatus 15 in advance, the media access control (MAC) address of the wireless setting apparatus 15 may be diverted, or a random character string may be set in the initial activation. In all cases, a wireless network can be constructed by reducing the work load of the user.

For reasons described above, the wireless setting apparatus 15 subsequently sets the wireless communication parameters to the wireless access point 6 (T5). Setting items to the wireless access point 6 are the SSID and the PSK, and the channel to be used need not necessarily be set.

For example, if the wireless X-ray imaging apparatus 100 as illustrated in FIG. 1 is exceptionally installed by extending over to adjacent X-ray rooms to operate a plurality of units of the X-ray sensors 1, the channel of the wireless access point 6 of each X-ray room can explicitly be set to avoid radio frequency interference when the plurality of the X-ray sensors 1 are used simultaneously. In this case, if a channel outside the channel range corresponding to the region code contained in the wireless access point 6 is set, RF wave output is disabled. Alternatively, the RF regulation of the region of use is complied by selecting the channel to be used within the channel range corresponding to the region code while ignoring the channel setting.

It is necessary, as described above, to set the wireless communication parameters also to the X-ray sensor 1. Thus, the wireless setting apparatus 15 transmits the wireless communication parameters to the entry apparatus 10 (T6). Accordingly, the entry apparatus 10 transmits the wireless communication parameters to the short-range wireless communication unit 11 of the X-ray sensor 1 (T7) by short-range wireless communication to reflect settings in the RF wave communication unit 5 in the end (T8). Items to be set here include the SSID, the PSK, the IP address (xif_ip) of the X-ray interface apparatus 4, the IP address (det_ip) allocated to the X-ray sensor 1, and the region code.

As described above, by setting the SSID and the PSK set to the wireless access point 6 to the RF wave communication unit 5, permission to access the wireless access point 6 can be obtained. Subsequently, as described above, the channel need not explicitly be specified to the wireless access point 6, the RF wave communication unit 5 performs a channel scan when connecting to the wireless access point 6 to search for the channel over which the wireless access point 6 can be connected.

The channel scan may be a passive scan that receives a RF wave from the wireless access point 6 for a fixed period to check the channel to be used or an active scan in which the RF wave communication unit 5 first transmits a RF wave to try to establish connection to the wireless access point 6.

At this point, the channel range of the channel scan is controlled by the region code set to the RF wave communication unit 5. As described above, the wireless access point 6 selects the channel to use from within the channel range corresponding to the region code. Similarly, the radio wave communication unit 5 identifies the corresponding channel range from the region code received by the short-range wireless communication unit 11 and performs a change scan within the range. The wireless access point 6 also is set the channel to use within the channel range corresponding to the same region code and therefore, communication can be established between the X-ray sensor 1 and the wireless access point 6 by the channel scan.

With the above sequence, wireless communication between the X-ray sensor 1 and the wireless access point 6 can be performed with RF wave settings corresponding to the region of use by pressing the switch 12 of the X-ray sensor 1.

The present invention can also be realized by executing the following processing. More specifically, software (a program) for realizing the functions of the above exemplary embodiments is supplied to a system or an apparatus via a network or various storage media and a computer (or a central processing unit (CPU) or a micro processing unit (MPU)) of the system or the apparatus reads and executes the program.

While the present invention has been described with reference to exemplary embodiments, it is to be understood that the invention is not limited to the disclosed exemplary embodiments. For example, although it has been described that the entry apparatus 10 is a device conforming to short-range wireless communication such as Infrared Data Association (IrDA). Short-range wireless communication is not limited to IrDA, but other communication standards or protocols such as Bluetooth®, RFID (Radio Frequency Identification), UHF and VHF may be also used. Accordingly, the scope of the following claims is to be accorded the broadest interpretation so as to encompass all modifications, equivalent structures, and functions.

This application claims priority from Japanese Patent Application No. 2010-182176 filed Aug. 17, 2010, which is hereby incorporated by reference herein in its entirety.

What is claimed is:

1. A communication apparatus used in an X-ray imaging system including an X-ray sensor and a wireless access point containing a region code and configured to perform RF wave wireless communication, the communication apparatus comprising:

a setting unit configured to acquire a region code, which is corresponding to the region code contained in the access point, and to set wireless communication parameters to within a range of a channel corresponding to the region code;

a transmitter configured to transmit the wireless communication parameters to the X-ray sensor by another communication different from the RF wave wireless communication; and a receiver configured to receive the image data from the X-ray sensor through the wireless access point, wherein the X-ray sensor is configured to transmit the image data to the wireless access point by the RF wave wireless communication based on the set wireless communication parameters.

2. The communication apparatus according to claim 1, wherein the wireless communication parameters set by the setting unit include a service set identifier (SSID), an encryption key, and channel information.

3. The communication apparatus according to claim 1, wherein the transmitter uses, as the another communication, one of Infrared Data Association, Bluetooth, Radio Frequency Identification, and TransferJet to transmit the wireless communication parameters to the X-ray sensor.

4. The communication apparatus according to claim 1, wherein the transmitter performs short-range wireless communication with the X-ray sensor, and the setting unit sets the wireless communication parameters in response to reception of a signal of the short-range wireless communication from the X-ray sensor.

5. An X-ray sensor capable of receiving wireless communication parameters from an entry apparatus and of transmitting image data by RF wave wireless communication via an access point, the X-ray sensor comprising:

a generation unit configured to generate an X-ray strength distribution as digital X-ray image data;

a communication unit configured to communicate with the entry apparatus by using another communication different from the RF wave wireless communication to acquire the wireless communication parameters in which a region code contained in the access point is included; and a RF wave communication unit configured to transmit the digital X-ray image data with the access point by the RF wave wireless communication using the wireless communication parameters.

6. The X-ray sensor according to claim 5, wherein the X-ray sensor does not perform the wireless communication by the RF wave communication unit until the wireless communication parameters reflecting the region code is set within the X-ray sensor.

7. A wireless communication system, comprising:
an access point storing a region code;
an X-ray sensor configured to generate digital X-ray image data;
a wireless setting apparatus configured to acquire a region code which is corresponding to the region code stored in the access point and to set wireless communication parameters to within a range of a channel corresponding to the region code;
an entry apparatus configured to transmit the wireless communication parameters to the X-ray sensor by another communication different from the RF wave wireless communication,
wherein the X-ray sensor wirelessly transmits the digital X-ray image data to the access point by RF wave wireless communication within the set wireless communication parameters.

8. The wireless communication system according to claim 7, further comprising an X-ray generation apparatus configured to illuminate the X-ray sensor with X-rays.

9. A communication method for a wireless communication system including an X-ray sensor capable of transmitting digital X-ray image data by wireless communication and an access point capable of receiving the digital X-ray image data by the wireless communication, the wireless communication method comprising:
acquiring a region code contained in the access point;
setting wireless communication parameters to within a range of a channel corresponding to the region code;
transmitting the wireless communication parameters to the X-ray sensor by another communication different from the RF wave wireless communication; and
wirelessly transmitting the digital X-ray image data from the X-ray sensor to the access point by RF wave wireless communication within the set wireless communication parameters.

10. A non-transitory computer-readable medium storing a computer-readable program to control a wireless communication system including an X-ray sensor capable of transmitting digital X-ray image data by wireless communication and an access point capable of receiving the digital X-ray image data by the wireless communication, the program causing a computer to:

acquire a region code contained in the access point;
set wireless communication parameters to within a range of a channel corresponding to the region code;
transmit the wireless communication parameters to the X-ray sensor by using another communication different from the RF wave wireless communication; and
wirelessly transmit the digital X-ray image data from the X-ray sensor to the access point by RF wave wireless communication within the set wireless communication parameters.

11. An X-ray sensor, comprising:
a generation unit configured to generate an X-ray strength distribution as digital X-ray image data;
a communication unit configured to communicate with an entry apparatus by another communication different from the RF wave wireless communication to acquire wireless communication parameters in which a region code contained in an access point is included; and
a RF wave communication unit configured to transmit the digital X-ray image data to the access point by RF wave wireless communication using the wireless communication parameters.

12. The communication apparatus of claim 1, wherein the setting unit is configured to acquire a region code which is the same as the region code contained in the access point.

13. The wireless communication system of claim 7, wherein
the wireless setting apparatus is configured to acquire a region code which is same as the region code contained in the access point.

14. The communication method of claim 9,
wherein the acquiring includes acquiring a region code which is the same as the region code contained in the access point.

15. The non-transitory computer-readable medium of claim 10,
wherein the program causes the computer to acquire a region code which is the same as the region code contained in the access point.

16. The communication apparatus of claim 1, wherein the setting unit is configured to acquire the region code from the wireless access point.

17. The X-ray sensor according to claim 5, wherein the communication unit uses, as the another communication, one of Infrared Data Association, Bluetooth, Radio Frequency Identification, and TransferJet to acquire the wireless communication parameters from the entry apparatus.

* * * * *